United States Patent [19]

Finney

[11] 4,387,705
[45] Jun. 14, 1983

[54] PENILE IMPLANT
[75] Inventor: Roy P. Finney, Tampa, Fla.
[73] Assignee: Medical Engineering Corporation, Racine, Wis.
[21] Appl. No.: 328,826
[22] Filed: Dec. 9, 1981

Related U.S. Application Data

[63] Continuation-in-part of Ser. No. 169,174, Jul. 15, 1980.
[51] Int. Cl.³ .................... A61B 19/00; A61F 5/00
[52] U.S. Cl. ............................ 128/1 R; 128/79; 3/1
[58] Field of Search ...................... 128/79, 1; 3/1

[56] References Cited
U.S. PATENT DOCUMENTS

| | | | |
|---|---|---|---|
| 3,835,857 | 9/1974 | Rogers et al. | 128/295 |
| 3,863,638 | 2/1975 | Rogers et al. | 128/295 |
| 4,187,851 | 2/1980 | Hauser | 128/295 |
| 4,204,530 | 5/1980 | Finney | 128/79 |

Primary Examiner—Stephen C. Pellegrino
Attorney, Agent, or Firm—Quarles & Brady

[57] ABSTRACT

A penile implant for assisting in retaining a urinary collection device on a penis includes an implant of biocompatible material having a ring with a generally D-shaped cross section with the belly of the D extending outwardly and an anchoring sleeve connected to the ring, said ring and sleeve are shaped and sized to be positioned circumferentially about a penis and implanted beneath the penile skin to provide a circumferential outwardly extending protuberance which assists in retaining an elastic urinary collection sheath upon the penis.

5 Claims, 6 Drawing Figures

PENILE IMPLANT

RELATED APPLICATION

The present application is a continuation-in-part of my earlier copending patent application Ser. No. 169,174 filed July 15, 1980.

FIELD OF THE INVENTION

The present invention relates to a penile implant and more particularly to a penile implant which is useful in retaining the flexible sheath of a urinal device in place on the penis of an incontinent male patient.

DESCRIPTION OF THE PRIOR ART

Incontinent male patients, such as those suffering from spinal cord injuries, often wear devices for the collection of urine. The urinary collection device most widely used with incontinent male patients is commonly called a "Texas Catheter" and it consists of a flexible condom-like sheath which is secured to the patient's penis and a tubular member which connects the condom-like device to a suitable urine receptacle. A device of this type is shown in the Rogers et al U.S. Pat. No. 3,835,857, granted Sept. 17, 1974.

One of the problems involved in the use of the "Texas Catheter" is that the sheath which depends upon its elasticity to stay in place can be accidently removed quite easily from the patient's penis without the patient being aware of its removal. Another Rogers et al patent, U.S. Pat. No. 3,863,638, discloses a liner pad which has an adhesive coating which clings to the penis and which is designed to retain the elastic sheath on the penis. Still another patent relating to a sheath liner useful for this purpose is U.S. Pat. No. 4,187,851.

Although the use of an adhesive coated sheath liner is an improvement on the use of the sheath itself in preventing accidental removal, it is not without disadvantages. For example, the liner normally has to be either placed on or removed from the penis of the patient by a person other than the patient. In addition, the liner and its adhesive layer can cause tissue irritation. Obviously, therefore, a need still exists for an improved means or method for securely attaching the sheath of a Texas catheter to the penis of an incontinent male patient.

In my earlier patent application Ser. No. 169,174 filed July 15, 1980, I disclosed a novel method for retaining the sheath of a urinary collection device upon the penis of an incontinent male which included implanting a D-shaped ring of biocompatible material underneath the penile skin of the distal end of the patient's penis. The implanted ring forms a protuberance which increases the external diameter of the penis and retains the flexible elastic sheath in place.

I have now developed an improved implant which provides advantages in addition to those provided by my earlier invention.

SUMMARY OF THE PRESENT INVENTION

It is an object of the present invention to disclose a novel method for retaining the sheath of a urinary collection device upon the penis of an incontinent male patient that does not require the use of liners.

It is another object of the present invention to disclose a penile implant which when surgically implanted provides a superior permanent means of retaining the flexible sheath of a urinary collection device in place.

The penile implant of the present invention includes a ring of soft, flexible, biocompatible material which is implanted underneath the penile skin at the distal end of the patient's penis. The ring preferably is generally D-shaped in cross section and it is implanted with the curved belly of the D extending outwardly. The improved implant of the present invention also includes an anchoring sleeve which is integrally connected to the ring and which preferably is provided with openings into which tissue can grow to anchor the implant in place. The sleeve has the same inner diameter as the ring and is in the form of a partial cylinder. The integral sleeve offers several advantages. For example, it makes it possible to use a softer material for the D-shaped ring because the sleeve can be used for anchoring; it also permits dispensing with the use of implanted support rods and minimizes the possibility of an unanchored ring eroding through the penile skin.

These and still other objects and advantages of the invention will become apparent to those skilled in the art from the description and the drawings which follow.

DESCRIPTION OF THE PREFERRED EMBODIMENT

Figure 1:
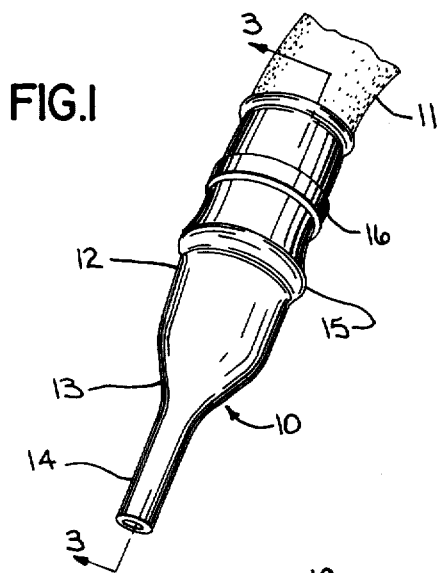
FIG. 1 is a perspective view of a penis with the implant of the present invention surgically implanted therein and a sheath of a urinary collection device in place.

Referring to FIG. 1, a sheath 10 of a urinary collection device is shown positioned upon a penis 11. The sheath 10 has a body portion 12 joined to a conical funnel like section 13 which terminates in a tube 14 which leads to a urine receptacle (not shown). The body portion 12 is of thin elastic material, such as latex rubber, which is capable of being rolled upon itself and then unrolled onto the penis 11 over a protuberance 15. As seen in FIG. 1, an elastic band 16 is positioned overlying the body portion of the sheath 10 at a point behind the protuberance 15. The use of the elastic band 16 is optional and is preferred when additional assurance is desired to insure that the sheath 10 will not be accidentally removed.

Figure 2:
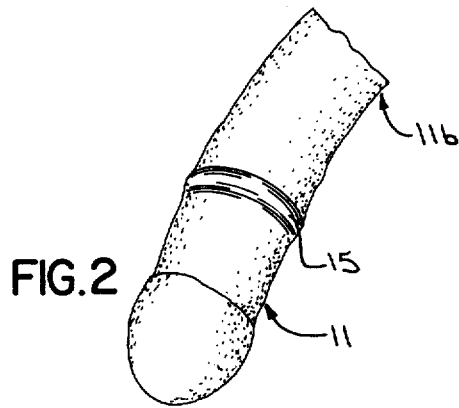
FIG. 2 is a perspective view of a penis with the implant surgically implanted therein but without the sheath.

In FIG. 2, the penis 11 with the protuberance 15 is seen without the sheath 10 and the elastic band 16. The protuberance 15 is formed by an implant 17 which has been surgically positioned under the skin 11a of the penis 11 as seen in FIG. 3.

Figure 3:
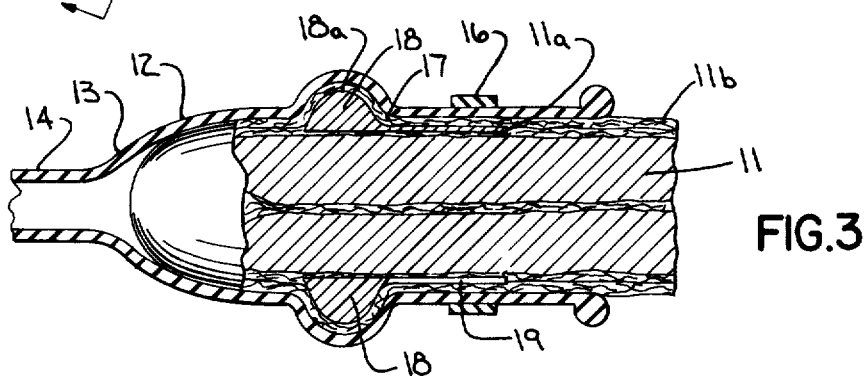
FIG. 3 is a partial sectional top plan view taken along the line 3—3 in FIG. 1.
Figure 4:
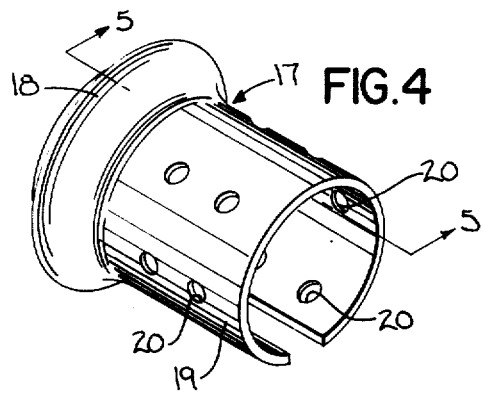
FIG. 4 is a perspective view of the implant of the present invention.
Figure 5:
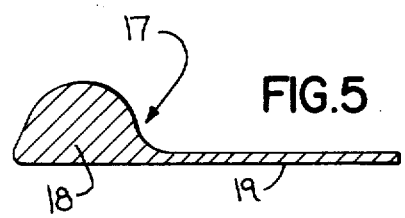
FIG. 5 is a cross sectional view of the implant taken along line 5—5 in FIG. 4.
Figure 6:
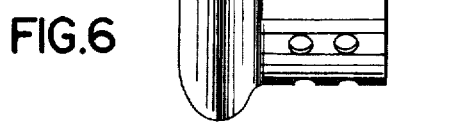
FIG. 6 is a bottom view of the implant.

Referring to FIGS. 3 to 6 it can be seen that the implant 17 has a ring portion 18 and an integral sleeve 19. The sleeve 19 is a partial cylinder and it is provided with openings 20 for tissue ingrowth. The ring portion 18 and the sleeve 19 are preferably molded as a single piece of a physiologically inert material such as medical grade silicone rubber. The ring portion 18 is preferably of a soft and flexible material and D-shaped in cross section. As seen in FIG. 3, the implant 17 is implanted beneath the penile skin with the curved or belly portion 18a of the D extending outwardly. The sleeve 19 which is preferably molded integrally with the ring 18 is of a less soft, more supportive material. When properly implanted the sleeve 19 extends beneath the skin 11a along the shaft of the penis above the corpra and toward the base 11b of the penis 11.

Medical grade silicone rubber is the preferred material for the implant 17 because it is biocompatible and it can be formulated to provide a material which possesses suitable tensile strength, stiffness and softness for the intended function. However, other materials possessing the desired properties also may be used.

The stiffness or softness of the material may be measured with a durometer, such as a Shore A durometer, which ascertains the depth of the penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension. A Scott Tensile Tester may be used to measure the stress which produces failure.

In order to minimize the possibility of its erosion through the penile skin, the ring portion 18 of the implant 17 is preferably formed of a material having a Shore A hardness of about 10 which is very soft and flexible. The sleeve 19 which provides the support for the implant 17 and prevents it from migrating should be of a relatively stiffer but still flexible material having a Shore A hardness of about 20. The ring portion 18 and the sleeve 19 are preferably covered with an outer layer of very soft silicone material and all edges are arced or curved to minimize tissue damage. If the patient is impotent as well as incontenent, a penile prosthesis to correct impotency such as a pair of composite penile rod implants of the type disclosed in U.S. Pat. No. 4,066,037 can be implanted in the corpra cavernosum.

The preferred method of implantation of the implant 17 will now be described. The penile skin is dissected together with the loose underlying areola tissue away from the Bucks fascia for approximately 2.5 cc. The appropriate anatomical measurements are made to select an implant having a ring and sleeve of proper size so that it can be properly positioned in contact with the Bucks fascia but not constrict it. The skin and loose areola tissues are then pulled over the implant and sutured to the skin or mucous membrane at the coronal sulcus. The implant, if desired, can be anchored in place with sutures before the incision in the penile skin is closed. A two layer closure using absorbable sutures may be used. After two weeks the sheath for collection of urine can be used.

It will be apparent to those skilled in the art that use of the implant of the present invention provides significant advantages over the previous methods of attaching the flexible elastic sheath of the urinary collection device to the penis. Prior art techniques are generally temporary and/or potentially unsanitary and/or require the assistance of others for proper placement of the sheath on the penis. In contrast, a patient with the implant of the present invention can simply and readily attach the condom-like sheath to his penis himself by unrolling the prerolled sheath over the distal end of the penis and the protuberance formed by the implant and, if desired, for extra security putting an elastic band in place. The protuberance formed by the surgical implantation of the implant effectively increases the diameter of the penis and thus provides a very effective means of retaining the elastic sheath in place. The new improved implant which is the subject of this application permits the penis to be freely movable and flaccid so that no pressure points develop which can cause tissue irritation or ring erosion.

It is to be understood that the foregoing description has been for purposes of illustration and that a number of modifications and changes may be made without departing from the spirit and scope of the present invention. For example, if desired one or more porous patches may be attached to the ring or sleeve portions of the implant to permit tissue ingrowth to help anchor the implant in place. Therefore, the invention is not to be limited by any of the specific embodiments described but only by the claims which follow.

I claim:

1. A penile implant comprising an implant of biocompatible material including a ring with a generally D-shaped cross section with the belly of the D extending outwardly and an anchoring sleeve connected to the ring, said ring and sleeve being shaped and sized to be positioned circumferentially about a penis and implanted beneath the penile skin to provide a circumferential outwardly extending protuberance which assists in retaining a urinary collection device upon said penis.

2. The implant of claim 1 which includes means on the sleeve for tissue ingrowth.

3. The implant of claim 1 in which the ring and sleeve are of silicone rubber.

4. The implant of claim 1 in which the ring is formed of silicone rubber of Shore A 10 hardness.

5. The implant of claim 1 in which the sleeve is of relatively stiff material having a hardness of Shore A 20.

* * * * *